(12) United States Patent
Zitoun et al.

(10) Patent No.: US 12,253,504 B2
(45) Date of Patent: Mar. 18, 2025

(54) HYDROGEN SENSORS FROM ORGANOMETALLIC PRECURSORS

(71) Applicant: BAR-ILAN UNIVERSITY, Ramat Gan (IL)

(72) Inventors: David Zitoun, Ra'anana (IL); Guy Rahamim, Petah Tikva (IL)

(73) Assignee: BAR-ILAN UNIVERSITY, Ramat Gan (IL)

( * ) Notice: Subject to any disclaimer, the term of this patent is extended or adjusted under 35 U.S.C. 154(b) by 1113 days.

(21) Appl. No.: 15/734,690

(22) PCT Filed: Jun. 6, 2019

(86) PCT No.: PCT/IL2019/050649
§ 371 (c)(1),
(2) Date: Dec. 3, 2020

(87) PCT Pub. No.: WO2019/234746
PCT Pub. Date: Dec. 12, 2019

(65) Prior Publication Data
US 2021/0231625 A1 Jul. 29, 2021

Related U.S. Application Data

(60) Provisional application No. 62/681,738, filed on Jun. 7, 2018.

(51) Int. Cl.
G01N 33/00 (2006.01)
G01N 27/12 (2006.01)
B82Y 30/00 (2011.01)

(52) U.S. Cl.
CPC ......... *G01N 33/005* (2013.01); *G01N 27/127* (2013.01); *B82Y 30/00* (2013.01)

(58) Field of Classification Search
CPC .... G01N 33/005; G01N 33/20; G01N 33/203; G01N 27/04; G01N 27/127; B82Y 30/00; Y10T 436/22; Y10T 436/25875
USPC ...... 422/83, 88, 90, 98; 436/73, 80, 84, 144, 436/149, 151, 181
See application file for complete search history.

(56) References Cited

U.S. PATENT DOCUMENTS

| | | | |
|---|---|---|---|
| 7,186,381 B2 * | 3/2007 | Penner ................. | G01N 27/127 977/773 |
| 7,340,941 B1 * | 3/2008 | Fruhberger .......... | G01N 29/036 73/24.01 |
| 7,791,150 B1 * | 9/2010 | Seal ..................... | G01N 27/127 257/467 |
| 8,683,672 B2 * | 4/2014 | Deshusses ........... | G01N 27/127 422/50 |
| 2007/0125153 A1 | 6/2007 | Visel et al. | |
| 2018/0356380 A1 * | 12/2018 | Ju ......................... | G01N 27/12 |
| 2019/0339227 A1 * | 11/2019 | Drmosh ................ | C23C 14/16 |

FOREIGN PATENT DOCUMENTS

| | | | |
|---|---|---|---|
| CN | 1797806 A | | 7/2006 |
| CN | 109250748 A | | 1/2019 |
| KR | 1020090022620 A | | 3/2009 |
| KR | 2010116428 | * | 11/2010 |
| KR | 101092865 B1 | | 12/2011 |
| KR | 101495422 B1 | | 2/2015 |
| WO | 2006/121349 A1 | * | 11/2006 |

OTHER PUBLICATIONS

Hafeezullah et al. Journal of Alloys and Compounds, vol. 616, Jul. 11, 2014, pp. 76-80.*
Peng et al. Nanotechnology, vol. 28, May 4, 2017, pp. 1-8.*
Yoo et al. Sensors and Actuators B, vol. 108, Feb. 5, 2005, pp. 159-164.*
Shanmugasundaram et al. The Journal of Physical Chemistry C, vol. 118, Mar. 15, 2014, pp. 6909-6921.*
Tamaekong et al. Sensors, vol. 9, Aug. 26, 2009, pp. 6652-6669.*
Rahamim et al. Sensors and Actuators B: Chemical, vol. 310, Feb. 7, 2020, pp. 1-9.*
Rahamim et al. Advanced Materials Interfaces, vol. 6, Aug. 12, 2019, pp. 1-8.*
International Search Report issued in Application No. PCT/IL2019/050649 on Sep. 18, 2019, 7 pages.
A. Manzo-Robledo et al., "Electro-oxidation of methanol in alkaline conditions using Pd—Ni nanoparticles prepared from organometallic precursors and supported on carbon vulcan", Journal of Nanoparticle Research, vol. 17, No. 12, Dec. 9, 2015, 8 pages.
Arvind B. Madavi et al., "Kinetics study of a palladium-nickle colloidal nanocatalyst synthesized by a wet-chemical method for reduction of nirophenol, nitroaniline, and 4-nitrobenzo-15-crown compounds", Particulate Science and Technology, vol. 35, No. 4, 2017, pp. 400-409.
Cuiling Li et al., "A universal approach to the preparation of colloidal mesoporous platinum nanoparticles with controlled particle sizes in a wide range from 20 nm to 200 nm", Physical Chemistry Chemical Physics, vol. 16, No. 19, Apr. 3, 2014, pp. 8787-8790.
Duy-Thach Phan et al., "Reliability of hydrogen sensing based on bimetallic Ni—Pd/graphene composites", International Journal of Hydrogen Energy, vol. 39, No. 35, Oct. 31, 2014, pp. 20294-20304.
Partial Supplementary European Search Report issued in Application No. 19814064.2 on Mar. 22, 2022, 15 pages.
Matsura et al. Sensors and Actuators (1988) 14:223-232.
Natalia J. S. Costa et al: "Organometallic Preparation of Ni, Pd, and NiPd Nanoparticles for the Design of Supported Nanocatalysts".

* cited by examiner

*Primary Examiner* — Maureen Wallenhorst
(74) *Attorney, Agent, or Firm* — CANTOR COLBURN LLP (57) ABSTRACT

The invention provides a sensitive and cost-effective hydrogen sensor manufactured by a simple method from organometallic precursors.

7 Claims, 11 Drawing Sheets

Fig.12B

HYDROGEN SENSORS FROM ORGANOMETALLIC PRECURSORS

CROSS REFERENCE TO RELATED APPLICATIONS

This application is a National Stage application of PCT/IL2019/050649, filed Jun. 6, 2019, which claims the benefit of U.S. Provisional Application No. 62/681,738, filed Jun. 7, 2018, both of which are incorporated by reference in their entirety herein.

FIELD OF THE INVENTION

The present invention relates to the field of hydrogen sensors, particularly the invention relates to producing hydrogen sensors by a simple and cost-effective process employing depositing metal nanoparticles containing palladium/nickel or platinum formed from organometallic compounds.

BACKGROUND OF THE INVENTION

Hydrogen ($H_2$) is a colorless, odorless and tasteless flammable gas. Moreover, from its unique physical properties, including high detonation sensitivity, low ignition energy (0.017 mJ), high combustion heat (142 kJ/g), wide flammability range (4-75%), and high permeability through most of the materials, one can understand the need and demand for special precautions, and the essential need for fast and accurate sensing of $H_2$ generation or accumulation to prevent explosions.

There are many areas where hydrogen sensing and monitoring act as an essential need, among them being chemical synthesis, metallurgical processes, nuclear reactors, coal mines, electric power plants, space applications, and fuel cells. In the latter, $H_2$ is brought to the customer for grid or mobile applications, including cars. It is generally accepted that the successful implementation of the international treaties aiming at limiting $CO_2$ necessitates breakthroughs in the hydrogen technology as an energy carrier, both for energy storage and electrochemical propulsion (fuel cells).

The main investigated material for hydrogen sensing is palladium (Pd). This metal reacts when exposed to $H_2$ by absorbing hydrogen, resulting in increased volume and a resistivity change. A need is felt to improve the detection limit of the sensors, as well as their selectivity, response time, reliability, and power saving. Regarding methods of producing hydrogen sensors, simpler and more cost-effective methods are needed. It is therefore an object of the invention to provide a novel hydrogen sensing system.

It is another object of this invention to provide novel hydrogen sensing materials by a simple and cost-effective method.

Other objects and advantages of present invention will appear as the description proceeds.

SUMMARY OF THE INVENTION

The invention provides a hydrogen sensor comprising metal nanoparticles as a resistive member in contact with two well conductive electrodes, said electrodes constituted by a gold film, and said nanoparticles consisting of palladium (Pd) and nickel (Ni) or of platinum (Pt), the metal nanoparticles obtained from organometallic compounds by reduction with hydrogen and optionally being mixed with nanoparticles of a semiconductor. Said nanoparticles have preferably a size of less than 20 nm; such as 10 nm or less, for example about 5 nm in average. Said gold film is preferably thinner than 200 nm, such as 100 nm or thinner, for example 90 nm or thinner, 80 nm or thinner, 70 nm or thinner, 60 nm or thinner, for example about 50 nm. Said semiconductor may comprise a doped semiconductor, for example comprising zinc oxide, indium oxide, tin oxide, zinc tin oxide, or indium tin oxide (ITO). The sensor of the invention can sense hydrogen at a concentration in air of 0.1% or less, for example 0.05% or less, 0.04% or less, 0.03% or less, 0.02% or less, for example about 120 ppm or about 100 ppm or about 80 ppm, or less than 80 ppm. Said resistive member preferably comprises palladium and nickel (Pd/Ni), Pd/Ni with ITO, or Pt with ITO. The sensor of the invention comprises in a preferred embodiment a resistive member comprising Pd/Ni in a molar ratio of from 2 to 200, such as from 4 to 100, preferably from 5 to 50, for example from 10 to 20.

In one aspect of the invention, the hydrogen sensor comprises Pd and Ni, usually in a weight ratio of between 10 and 100. In another aspect of the invention, the hydrogen sensor comprises a metal selected from Pd/Ni mixtures and Pt with a semiconductor, wherein semiconductor and said metal are in a weight ratio of from about 1 to about 200; in some embodiments, the sensor comprises 0.5-60 wt % Pd/Ni and 40-99.5 wt % ITO, for example 5-10 wt % Pd/Ni and 90-95 wt % ITO; in other embodiments, the sensor comprises 5-10 wt % Pt and 90-95 wt % ITO.

The invention is directed to a method of producing a hydrogen sensor comprising metal nanoparticles as a resistive member in contact with two well conductive electrodes, said metal selected from palladium with nickel (Pd/Ni) and platinum (Pt), said nanoparticles obtained from organometallic compounds by reduction with hydrogen and optionally being mixed with semiconductor nanoparticles, and said electrodes constituted by a gold film, comprising at least the following steps i) providing an organometallic palladium, preferably a Pd0 complex; providing an organometallic nickel, preferably Ni0 complex; mixing said components in a molar ratio Pd/Ni of from 5 to 50, in a suitable solvent, preferably mesytilene, possibly containing a surfactant, preferably amine, such as aliphatic amine; ii) mixing with hydrogen at a temperature from 0° C. to 200° C., preferably between ambient and 80° C., thereby obtaining a black Pd/Ni nanoparticles dispersion; iii) providing a pad coated with a gold film and creating a channel in said film to separate the film into two parts to serve as electrodes; and iv) depositing said nanoparticles dispersion to fill said channel and to contact said two gold film parts (electrodes), and removing the solvent. Said step iv) may comprise layering said nanoparticle dispersion in a desired geometric pattern onto a glass slide coated with gold, and removing the liquid. In one preferred aspect, ITO nanoparticles are admixed into the dispersion obtained in step ii). Said $Pd^0$ complex is, in one embodiment of the invention, bis(dibenzylideneacetone) palladium(0). said $Ni^o$ complex may be bis(1,5-cyclooctadiene) nickel(0). Said amine may advantageously be hexadecylamine. Said $Pd^o$ complex and $Ni^o$ complex usually have a total concentration of from 0.03 to 30 wt %, such as between 0.2 and 20 wt %. Said depositing may include a technique selected from the group consisting of spin, dip, drop, spray coating, and laser induced micro bubble techniques. Said depositing preferably includes a laser induced micro bubble technique.

The invention provides a nanoparticles dispersion for use in preparing a simple and cost-effective hydrogen sensor, comprising from 0.01 to 10 wt % nanoparticles, such as 0.1 to 5 wt %, for example from 0.2 to 4 wt %, such as 1 wt %, having an average size of less than 50 nm, such as less than 40 nm, for example less than 30 nm, preferably less than 20 nm, such as less than 10 nm, for example about 5 nm, and consisting of Pd and Ni in a molar ratio of from 5 to 50. Usually, Pd and Ni are in a weight ratio of from about 1 to about 100. In another aspect, the invention provides a nanoparticles dispersion for use in preparing a simple and cost-effective hydrogen sensor, comprising from 0.01 to 10 wt % nanoparticles, such as 0.2 to 4 wt % nanoparticles having a size less than 10 nm and consisting of ITO and Pd/Ni in a weight ratio of about 1 to 200.

In one aspect, the invention provides a method of producing the hydrogen sensor of claim 1, comprising at least the following steps i) providing an organometallic platinum, preferably a $Pt^0$ complex; mixing in a suitable solvent, preferably mesytilene, possibly containing a surfactant, preferably amine; ii) mixing with hydrogen at a temperature from 0° C. to 200° C., preferably between ambient and 80° C., thereby obtaining a black Pt nanoparticles dispersion; iii) mixing with ITO nanoparticles at a temperature of from 0° C. to 200° C., such as between ambient and 80° C., thereby obtaining a black Pt/ITO nanoparticles dispersion; iv) providing a pad coated with a gold film and creating a channel in said film to separate the film into two parts to serve as electrodes; and v) depositing said nanoparticles dispersion to fill said channel and to contact said two gold film parts (electrodes), and removing the solvent. Said $Pt^0$ complex may comprise tris(dibenzylideneacetone) diplatinum$^0$. Said amine mat be hexadecylamine. Said depositing may include a technique selected from the group consisting of spin, dip, drop, spray coating, and laser induced micro bubble techniques. Said depositing preferably includes a laser induced micro bubble technique. Said $Pt^0$ complex may have a concentration of from 0.03 to 30 wt %, such as between 0.2 and 20 wt %.

The invention provides a stock nanoparticles dispersion for use in preparing a simple and cost-effective hydrogen sensor, comprising from from 0.01 to 10 wt % nanoparticles, such as 0.1 to 5 wt %, for example 0.2 to 4 wt % such as about 1 wt %, having an average size of less than 50 nm, such as less than 40 nm, for example less than 30 nm, preferably less than 20 nm, such as less than 10 nm, for example about 5 nm, and consisting of PTO and Pt in a weight ratio of from about 1 to about 200.

The sensor of the invention may sense hydrogen in a broad range of concentrations. In a preferred embodiment, the sensor may sense hydrogen at a concentration of less than 4%, such as less than 3% or less than 2% or less than 1%, such as 0.5% or less in a mixture with air, for example 0.25% or less, such as 0.2% or less, 0.15% or less, 0.1% or less, 0.05% or less. The sensor of the invention may sense hydrogen at a concentration of 0.04% or less, such as 0.03% or less, 0.02% or less, and 0.01% or less, for example about 100 ppm, or about 50 ppm or less.

BRIEF DESCRIPTION OF THE DRAWINGS

The above and other characteristics and advantages of the invention will be more readily apparent through the following examples, and with reference to the appended drawings, wherein:

FIG. 6. shows sensors response to $H_2$ at a concentration between 0.5% and 0.01% at 0.5V bias (FIG. 6A), stability tests of the signal at 0.05% of $H_2$ (FIG. 6B), and 0.01% of $H_2$ (FIG. 6C);

FIG. 8. shows the colloidal deposition between the two electrodes.

FIG. 11. shows the PdNi-ITO sensor response for the exposure to $H_2$ in ambient air; 11A presents the sensor behavior to a range of $H_2$ concentrations in air of between 5% and 0.007%; 11B shows the sensor behavior for a repeating exposure to $H_2$ mixtures having a concentration of between 0.4% and 0.04%; and FIG. 12. shows the Pt-ITO sensor response to the exposure to $H_2$ in ambient air; 12A presents the sensor behavior in a range of $H_2$ concentrations in air of between 4% and 0.0125%.

DETAILED DESCRIPTION OF THE INVENTION

It has now been found that a simple synthetic pathway employing organometallic precursors combined with a simple deposition method provides an efficient hydrogen sensor produced in a cost-effective way.

Various methods have been employed for producing sensors by deposition, including e-beam lithography, electrode-position, sputtering, spin-coating, microwave irradiation etc.; conventional synthetic paths for hydrogen sensors and sensor's active materials are quite expensive, time consuming, require sophisticated and expensive tools, and have many synthetic steps and/or extreme conditions (pressure/temperature); not only better sensor's activity is needed, but also improved processes for their production.

The procedure according to the invention relies mainly on two aspects: the synthetic pathway and the deposition method, both being employed in a simpler, cheaper and more efficient way. Moreover, the simple deposition method according to the invention allows to work in open atmosphere and at room temperature, enabling various deposition geometries, and eliminating the need of annealing/sintering the deposition product. All these benefits combine into a cheap, simple, robust, and efficient method for hydrogen sensors production, resulting in sensors with superb sensing behavior, overcoming drawbacks of other methods.

Figure 1:
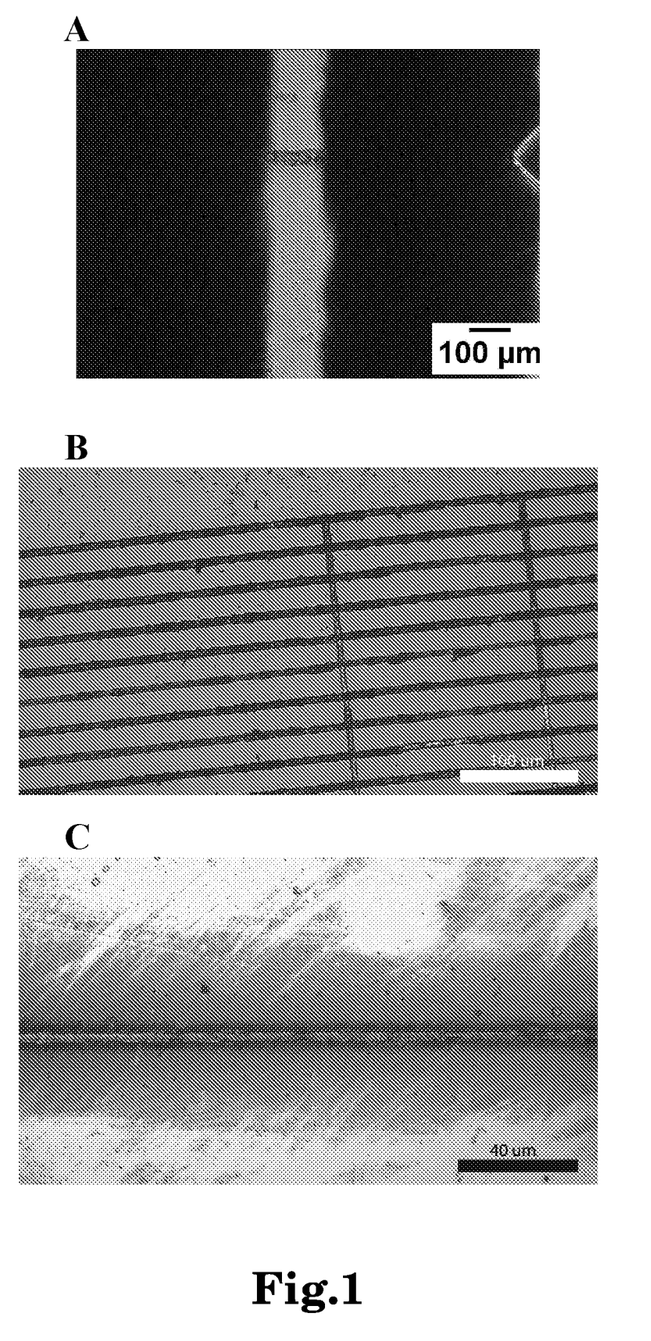
FIG. 1. shows light microscope images demonstrating ability of the method according to the invention to design specific sensor geometries, including stripe (1A), mesh (1B), and layer (1C); the length of the abscissa in 1A and 1B is 100 μm and in 1c is 40 μm.

In an important aspect of the invention, the synthetic part employs organometallic complexes. The combination of features employed by the invention results in a number of advantages. The use of organometallic complexes is associated with lower energetic barrier and, moreover, the synthesis requires only the presence of a reducing material advantageously constituted by gaseous hydrogen. Regarding the deposition part, several alternative coating techniques were found to be advantageous in the combination according to the invention, including spin, dip, drop, spray coating, and also laser induced micro bubble techniques (LIMBT). The nanoparticles deposition and the annealing step are achieved in one integrated stage, while preferably employing the LIMBT technique: focused laser beam is absorbed by nanoparticles (high localized heating) creating a micro-bubble causing convection of near nanoparticle into the glass slide, resulting in their deposit, in line with the laser beam moving direction. Moreover, the localized heating acts also as sintering process. Furthermore, the combination according to the invention enables designing specific sensor geometries, as demonstrated in FIG. 1, including stripes, meshes, films, and others. No complex and expensive lithography technique is used. In one preferred embodiment, the invention employs stock dispersion compositions (Pd, Pd/Ni, ITO, Pt, Pt/ITO etc.) which are synthesized from organometallic precursors at room temperature.

The main steps in producing the organometallic based nanoparticle dispersion are as follow: regarding Pd/Ni, Pd based organometallic complex is mixed with Ni based organometallic complex in a metals mole ratio of preferably from about 5 to about 50 (the amount of Pd in moles divided the amount of Ni in moles). For keeping the particles size in the nano-level, a surfactant is added preferably in at least a molar amount relatively to Pd, for example in about a double amount. For single metal nanoparticles suspensions (Pd, Pt etc.), the main steps are analogous. The suspension comprises a solvent with a relatively high boiling point. The dispersion is reduced by hydrogen (for example 1 bar). The nanoparticles obtained in the previous step are deposited on top of glass-slide, coated with Au/Cr (100/5 nm thick layer) and micro-scratched ("dewetting") by high power laser (5 W). The gap separates the Au/Cr coating into two parts and is used as the depositing area for said nanoparticles. The nanoparticles consist of Pd/Ni, or Pd/Ni with a semiconductor, or Pt with a semiconductor; the semiconductor comprising, for example, indium tin oxide (ITO). Preferably, LIMBT technic under ambient temperature/pressure is employed. The thickness of the deposited nanoparticles layer depends on the laser power, periodicity, and modulation, and usually is from 0.1 to 5 µm, such as from 0.2 to 2 µm, for example between 0.3 and 1.5 µm. The glass slide, with two gold film parts as electrodes and the nanoparticles deposited in between, is connected to potentiostat using Cu wires and silver paste or Cu tape. The measured resistivity (with no $H_2$ presence) varies usually between ohms and megaohms. The measured parameter, current, provides the desired change in the resistance of the sensor in the presence of $H_2$. The sensor employs calibrating, namely determining resistivity versus hydrogen concentration; clearly, the resistive member of the sensor, comprising the nanoparticles, contributes to the measured resistance much more than the electrodes, comprising the gold film.

In one aspect, the invention relates to a simple method of producing a hydrogen sensor form organometallic precursors. In another aspect, the invention relates to a simple sensor which exhibits a surprisingly sharp response time and a high output amplitude even at very low hydrogen concentrations. The sensor of the invention may sense hydrogen in a concentration of 0.1% or less, such as 800 ppm or less, 700 ppm or less, 600 ppm or less, 500 ppm or less, 400 ppm or less, 300 ppm or less, 200 ppm or less, 100 ppm or less, for example about 100 ppm or about 70 ppm. In some embodiments, the sensor of the invention senses hydrogen in air at a concentration of 70 ppm or less, such as 60 ppm or less, for example about 50 ppm, or 50 ppm or less.

Fabrication methods described so far do not enable controlled formation of desired micro-patterns. The invention now provides a method of forming desired conductive micropatterns for hydrogen sensing from colloids formed of organometallic precursors. The invention provides a process for manufacturing reproducibly working metal or semiconductor-metal based hydrogen sensors.

The process of the invention employs a step of reacting organometallic precursors, preferably Pd, Ni, and Pt, usually at ambient temperature, yielding a colloidal ink of nanoparticles containing Pd or Pd/Ni or Pt, to be possibly combined with semiconductor nanoparticles, such as ITO nanoparticles. This organic based ink displays a relatively high metal content, such as for example around 1 wt % or more, and a storage stability of several months. While employing modulated LIMBT, micro droplets of the above colloidal liquid—ink—are deposited on a gold-coated glass slide, thereby forming wires on the slide exhibiting sensor properties. The sensors are tested in air at room temperature to assess the sensitivity and reaction time in a real environment. An optical microscope may monitor the deposition—"writing process"—and a multimeter may determine the conductance of the sensor provided by the manufacturing process. The process of the invention provides sensors showing high reproducibility and fast response time, when measured in air at room temperature. The sensors according to the invention show excellent performance in terms of response, response time stability, and a low detection limit which goes down to about 100 ppm of $H_2$.

The invention provides a new sensor and a manufacturing procedure for making it, comprising steps of preparing organometallic based nanoparticles and employing modulated LIMBT. The procedure is relatively simple and reliable, obviating numerous washing steps and employing a colloidal solution which is practically very stable; even a small-scale synthesis described herein suffices to provide hundreds of sensors. The employed LIMBT is effective in providing conductive functional systems, while preserving nanoscale dimensions of the particles. The sensors display excellent sensitivity in a wide range of $H_2$ concentrations, with a detection limit below 100 ppm and with a clean and stable signal, and with a response time of seconds.

The method of the invention thus includes writing with organometallic precursor-based ink comprising laser-induced micro bubbles, thereby creating desired micro pattern to function as a hydrogen sensor which has a superior sensitivity and reliability.

The invention will be further described and illustrated by the following examples.

EXAMPLES

Materials

Mesytilene (99+%) was acquired from ACROS and dried ($H_{H2}O<50$ ppm). Hexadecylamine (HDA, 90%) has been dried, degassed and stored in a nitrogen glovebox. Bis(1,5-cyclooctadiene) nickel(0), Ni(COD)$_2$ (STREM, 98%), and bis(dibenzylidene acetone) palladium(0), Pd(dba)$_2$ (STREM, 98%) were used without further purification in the glovebox. Tris(dibenzylideneacetone) diplatinum(0), Pt2 (dba)3 (STREM, 98%) was used without further purification in the glovebox. The following materials were also employed: indium(III) acetate (ALDRICH, 99.99%), tin(II) 2-ethylhexanoate (SIGMA, 92.5-100%), n-octyl ether (J&k-scientific GmbH Ltd, 96%), oleylamine (ACROS, 80-90%), n-octanoic acid (ACROS, 99%). Hydrogen gas (99.999%) was purchased from Maxima.

Pd/Ni Nanoparticles Synthesis

Figure 2:
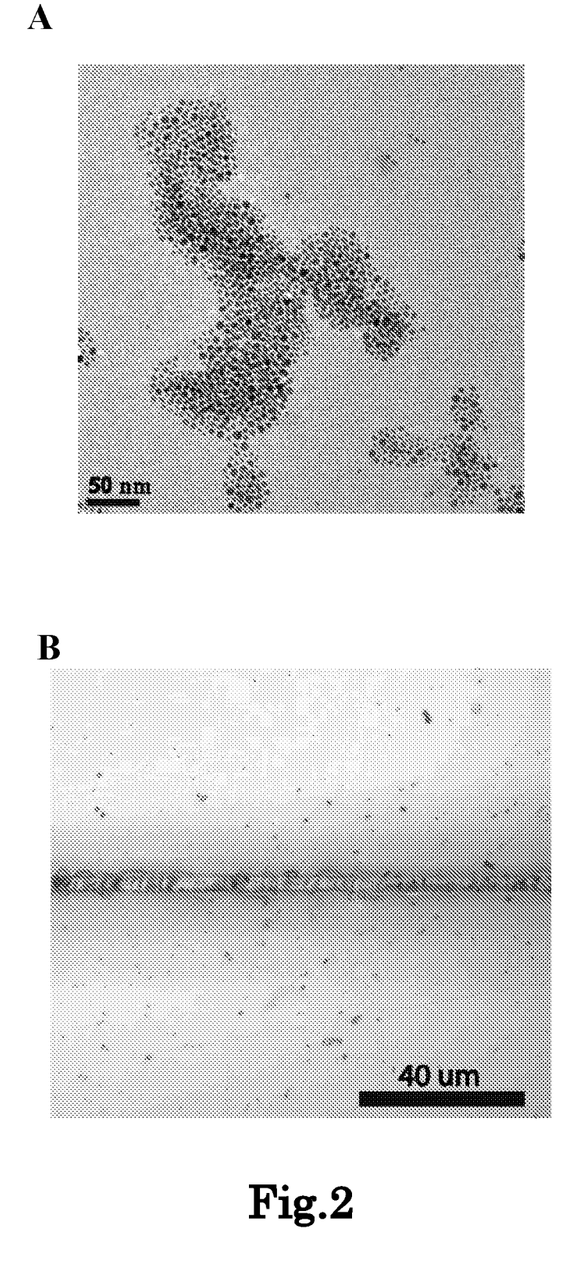
FIG. 2. shows (2A) TEM image of PdNi nanoparticles after performing the synthesis procedure, and (2B) light microscope image during the process of deposition; the length of the abscissa in 2A is 50 nm and in 2B 40 μm.

Inside a pressure bottle equipped with gauge meter, containing a stirring magnet, dissolved were 57.5 mg of $Pd(dba)_2$, 1.37 mg $Ni(COD)_2$ and 48.0 mg of HDA as surfactant, in 1.30 ml of mesytilene. All the preparation was performed inside the $N_2$ glovebox. The glass flask was then pressurized with 1-3 bar (gauge) of hydrogen and the mixture stirred at a constant temperature of about 35° C. for up to 12 minutes. The purple suspension turned black which gave an indication for the colloid formation. The average size of the nanoparticles formed by this synthesis was about 5 nm (FIG. 2a). The dispersion (also called colloid solution) was used as described below in the LIMBT section.

In some embodiments, the above formed nanoparticles were further mixed with a metal semiconductor, for example a freshly synthesized indium tin oxide (ITO).

Pt Nanoparticles Synthesis

Inside a pressure bottle equipped with gauge meter, containing a stirring magnet, dissolved were 40 mg of $Pt_2(dba)_3$ and 17.7 mg of HDA as surfactant in 1.60 ml of mesytilene. All the preparation was performed inside the $N_2$ glovebox. The glass flask was then pressurized with 3 bar (gauge) of hydrogen and the solution stirred at a constant temperature of about 35° C. for up to 15 minutes. The dispersion was used as described below in the LIMBT section.

Figure 9:
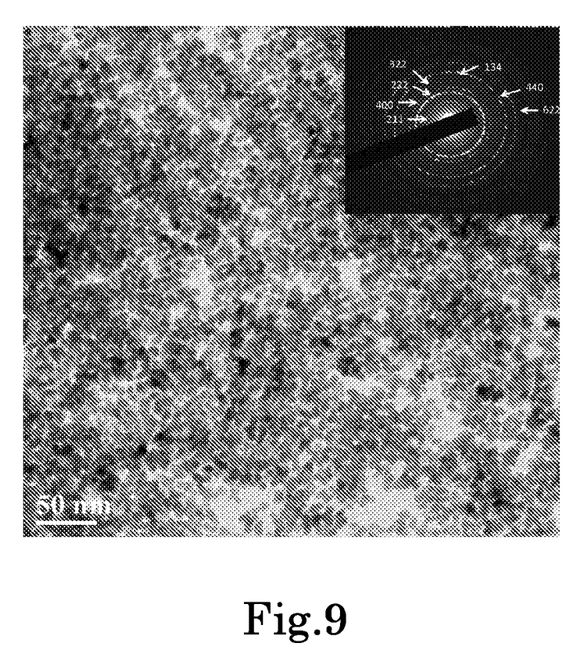
FIG. 9. shows HRTEM image of the ITO nanoparticles; the abscissa is 50 nm.

ITO nanoparticles synthesis Inside a glass flask, containing a stirring magnet, added were 1.2612 gr of indium(III) acetate, 0.2016 gr of tin(II) 2-ethylhexanoate suspended in 40 ml of n-octyl ether with 2.282 ml of n-octanoic acid and 13.16 ml of oleylamine. The suspestion was stirred at 80° C. under vacuum with reflux for 30 min, heated 1 hr at 150° C. under $N_2$, than the temperature was increased up to 280° C. (still under $N_2$ atmosphere), and then the suspension was purified using centrifuge for separation of the fluid and solids (nanoparticles) and suspended in 10 ml ethanol. The suspension was centrifuge again, with 5000 rpm and 10° C., for 20 minutes. Ethanol was replaced with mesytilene for mixing with other nanoparticle, such as PdNi or Pt. FIG. 9 shows HRTEM of the synthesized ITO nanoparticles.

Laser Induced Micro Bubble Technique

Square contact pads, 0.4 cm*0.4 cm in size, were fabricated by evaporating 5 nm of Cr followed by 100 nm of Au on a glass slide (BESTEC thin film evaporator). The process was performed in room temperature, the preliminary pressure was 0.003 pbar and the working pressure was 3 pbar. The materials purity for the Au and the Cr are 99.99 and 99.95, respectively. These pads were used as electronic contacts for the sensor.

LIMBT was employed by using COHERENT, Verdi™ G-Series, 532 nm, 5 W laser. The procedure is to inject several µl of the nanoparticles dispersion on top of the pads and perform the deposition process and then activate the laser setup as follow:

| Power (W) | 0.15-0.5 |
| Modulation (kHz) | 3 |
| Stage velocity (mm/sec) | 0.015-0.03 |
| Pulse | On: 0.08 Off: 0.25 |

The whole procedure is done under light microscope, where the laser beam enters from below of the slide. The glass slide was put on the computer-controlled microscope stage, MARZHAUSER, MFD Eclipse Ti, which was moved in a path controlled by operator in real time, with a stage velocity set to 15-30 µm/s. By varying the stage velocity and power, the deposition morphology and thickness were controlled. After performing the deposition, the glass slide is washed by ethanol and dried under $N_2$ flow, then measuring resistivity (checking the deposition). The pads "scratching" procedure was performed by high power (5 W), drawing a 3 µm wide channel gap in the middle and across the whole of each gold pad. Each gold pad was thus divided into two electric contacts 3-4 µm apart. After drop casting 10 µl of the as prepared nanoparticles dispersion in mesytilene on the Au pads, modulated LIMBT was used for material deposition along said gap. The optical system consists of an optically inverted microscope (Nikon, Eclipse Ti-U) with a 40× objective lens (0.6 NA, Nikon) attached to the laser. Laser modulation is performed by mechanical means (optical chopper-MC1F100, Thorlabs) and is set to 3 kHz with 50% duty cycle. A mechanical shutter was used (SH05, Thorlabs) and was set to open every 0.08 s and then close for 0.25 s. The laser power was set to 0.15-0.5 W.

The experiments were recorded using a CMOS camera (DPCAM 6CHDMI, DeltaPix). A multimeter (TENMA, 727740) was used to measure the sensor's conductance during the micro fabrication process. After performing the deposition, the glass slide is washed by ethanol and dried under a flow of $N_2$.

Figure 10:
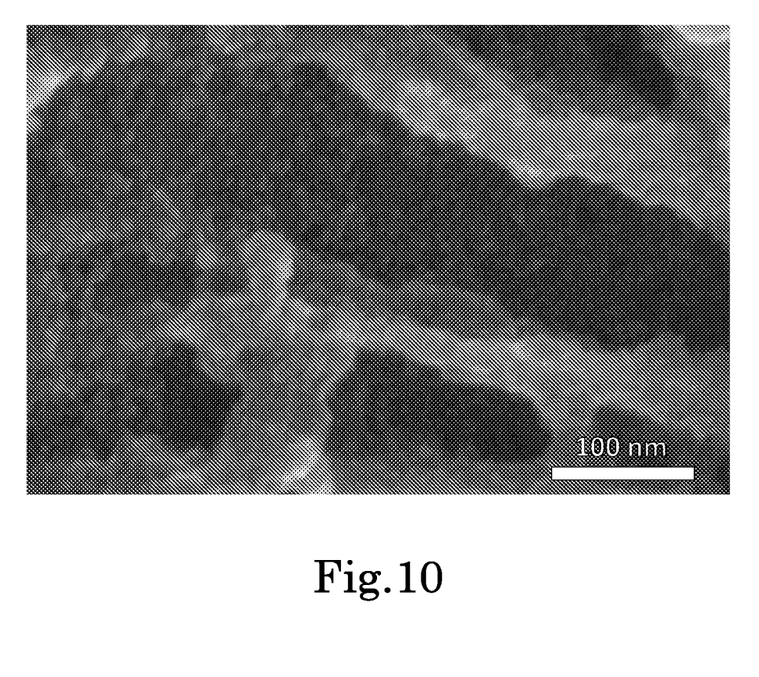
FIG. 10. shows HRSEM image of the Pt-ITO surface, after the deposition; the abscissa is 100 nm.

Said gap dividing the gold pad into two electrodes was thus formed by metal dewetting using a 532 nm laser. It can be noted that the light absorption of the dispersion is essential for the process since LIMBT requires light absorption of the colloidal dispersion in order to form a microbubble by heating. Therefore, the black color of a colloidal dispersion, such as the $Pd_{0.9}Ni_{0.1}$, is suitable. As the laser beam was focused at the liquid/substrate interface, the colloidal dispersion strongly absorbed the beam, causing local temperature increase of the solvent. The solvent's vapor pressure rose until a microbubble was formed. The temperature gradient between the top and bottom of the microbubble led to formation of convection flows, causing pinning of the NPs at the contact line between the microbubble and the substrate. The motorized stage led the deposition to occur along the gap between the electrodes, see FIG. 8A for the PdNi sensor and FIG. 10 for the Pt-ITO sensor.

The optimization of the LIMBT modulation parameters (power, stage velocity, duty cycle) was determined by connecting the Au pads to a multimeter and measuring the conductivity of the deposited material in real time, until it reached the desired value.

Figure 8A:
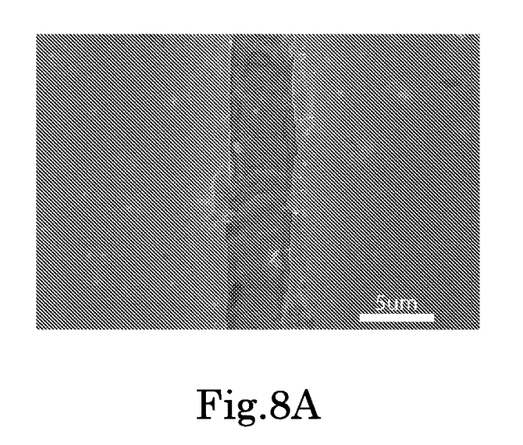
FIG. 8A is a SEM image of the deposition between the two electrodes.
Figure 8B:
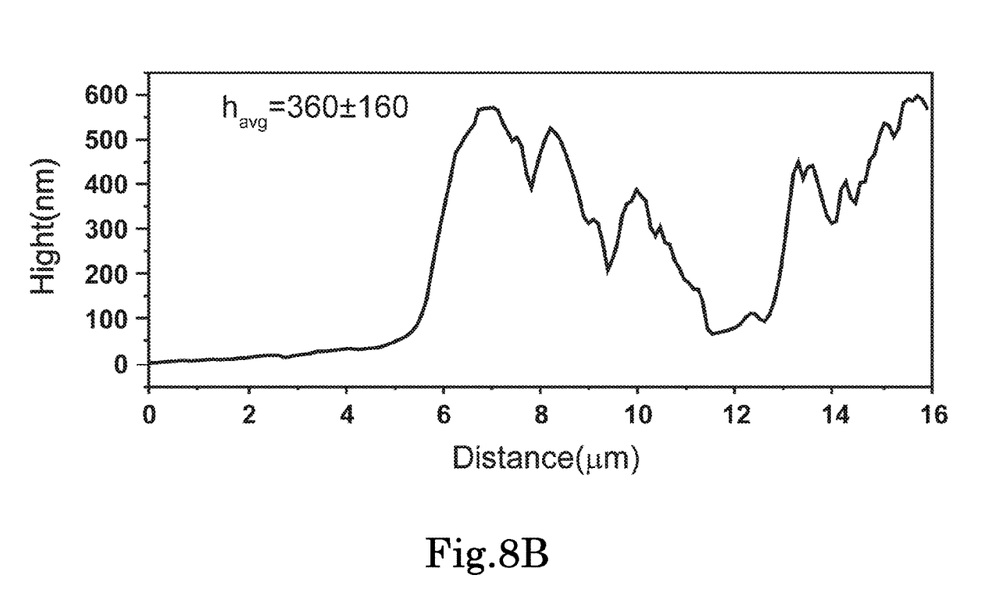
FIG. 8B is a line-scan of the deposited layer height provided by the AFM (atomic force microscopy)

The layer was observed by scanning electron microscopy (FIG. 8A). It consists of nanoscale particles, pointing at the successful assembly of conductive layers directly from $Pd_{0.9}Ni_{0.1}$ colloidal dispersion, i.e. without further sintering. Atomic force microscopy (AFM) gives the height profile of the deposited layer. FIG. 8B shows a line scan of the Pd/Ni sensor layer's thickness. The average thickness of 360±160 nm reveals the mechanism of modulated LIBMT deposition process. The LIBMT assisted colloidal fabrication protocol yields sensing layers with a broad range of initial resistivity. Before activation, the initial resistance can vary from several ohms up to M-ohms. The sensor activation is carried out through exposure to hydrogen.

Sensor Production

Figure 4:
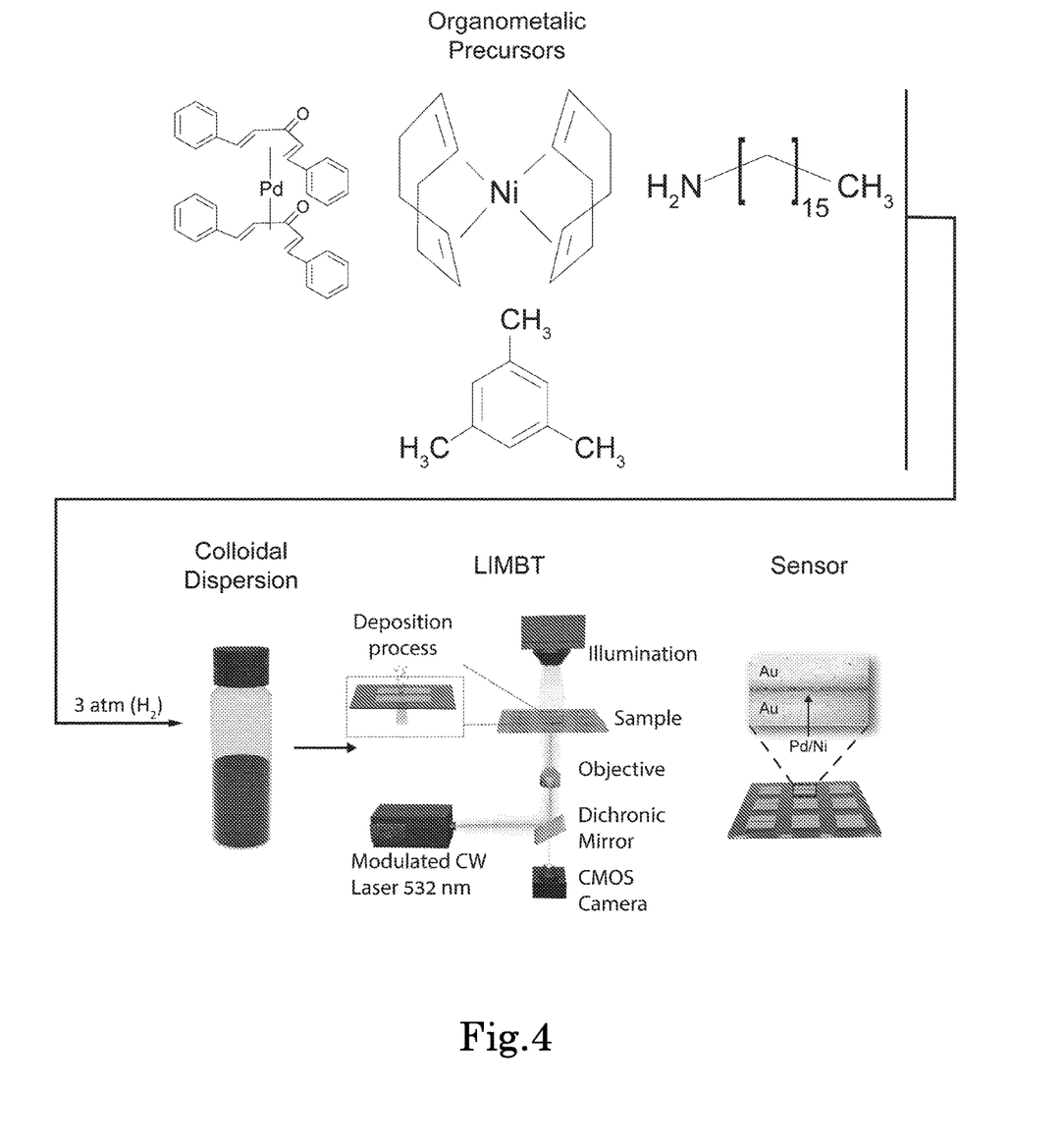
FIG. 4. shows the overall manufacture.
Figure 5:
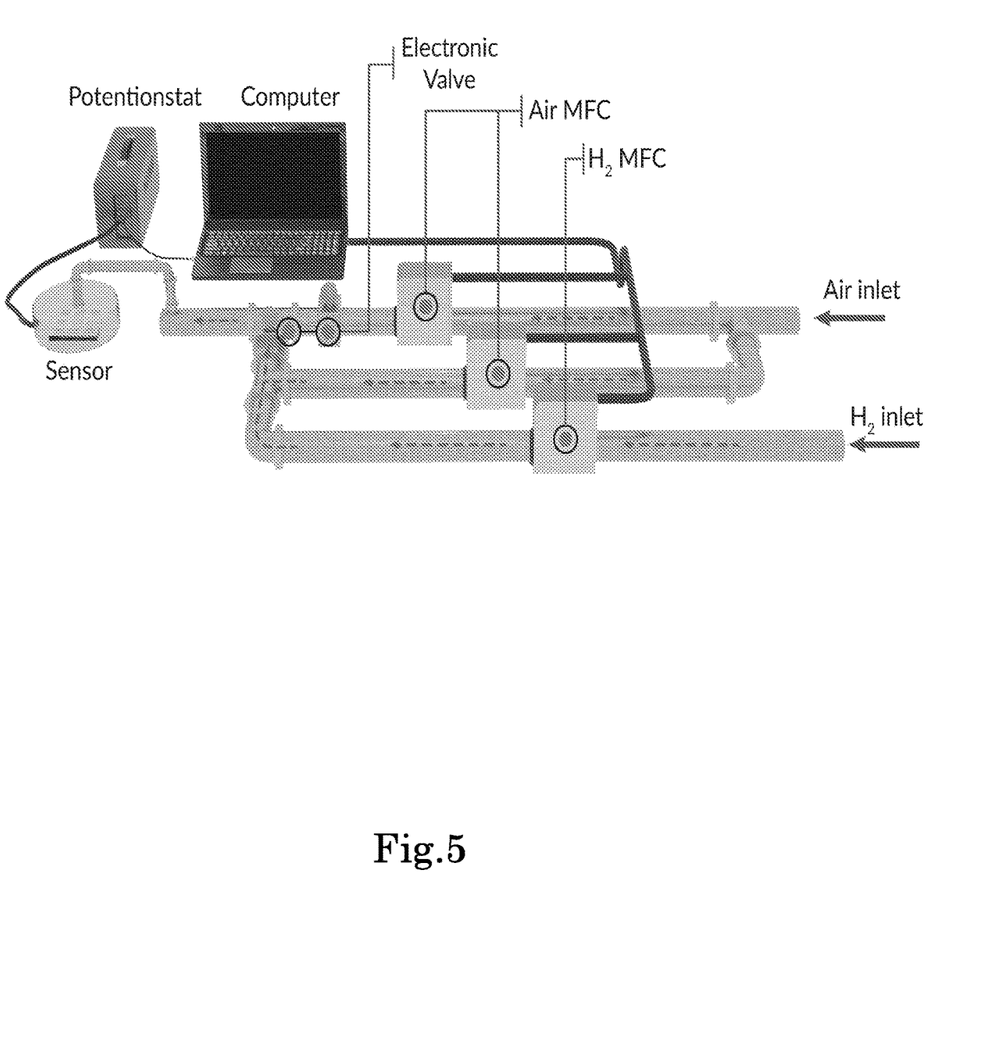
FIG. 5. schematically shows sensing bench-testing system.

FIG. 4 is a flowchart showing two manufacturing steps: organometallic-based synthesis of Pd/Ni colloids and laser-induced deposition; FIG. 5 schematically shows a bench-testing system according to the invention. The organometallic precursors easily decompose under hydrogen through the hydrogenation of the ligands and release the metal centers in the colloidal solution. The reaction occurs at low temperature and in a short time which enables the homogeneous nucleation of small nanoparticles. The metal weight concentration in the dispersion is set to be about 0.9 wt %, a relatively high value in the field of metal nanoparticles in organic solvents. Preferred surfactants in a method according to the invention comprise alkylamines, such as for example HAD, as they can be easily displaced or removed during the formation of the particles, in contrast with others, for instance alkylthiols, which may strongly bind to the surface of Pd. The long chain alkylamines stabilize the colloidal dispersion for months and facilitate the formation of small particles. The nanoparticles (NPs) are characterized by transmission electron microscopy (TEM), energy dispersive X-Ray spectroscopy (EDS) and X-ray diffraction (XRD). The nanoparticles are well dispersed and homogeneous in size (FIG. 2A—the PdNi nanoparticles). The particle size dispersion (PSD) was derived from the ImageJ software analysis of TEM images (300 particles), and the colloids displayed, in some tests, a lognormal PSD of 4.6±1.4 nm. The EDS measurements on the NPs confirm the stoichiometry with a molar metallic ratio of $Pd_{0.9}Ni_{0.1}$. The XRD showed the presence of a single phase. The lattice parameters were very close to face centered cubic (FCC) Pd (JCPDS #05-0681; Fm-3m, a=3.8902 Å: red lines) and did not show the presence of FCC Ni (JCPDS #04-0850; Fm-3m, a=3.5238 Å: blue lines). The two metals formed an alloy. The very small particle size and mild reaction conditions explain the formation of a disordered statistical alloy.

After the short synthesis (12 minutes), the colloidal suspensions were stored without any further treatment or purification. The yield was closed to 100% and the colloidal dispersion ready to use for months.

Sensing Measurements

For testing the sensor performances, a small volume testing chamber has been built, connected to mass flow controllers (MFCs, Bronkhorst, FG-201CV and F-200CV), for controlling the gases flow rates. The sensor was placed inside the chamber and electrically connected to a potentiostat (Bio-Logic, sp-50) for measuring the electrical signals during the tests. The whole components were controlled, monitored and data logged using labview programs (for synchronized data logging). For the response time measurement, two electrical valves (HAM-LET, UF20) were added to the testing system for preventing $H_2$ leaking originated from the MFCs, these leaks resulted in incorrect signals ("pre-response"). The valves were placed with minimal length from the testing tube. The electrical valves were activated (opened) after the MFCs response stabilized at the wanted flow rate. The electrical valves operation was synchronized with the rest of the testing system components (the MFCs and the potentiostat).

Figure 3:
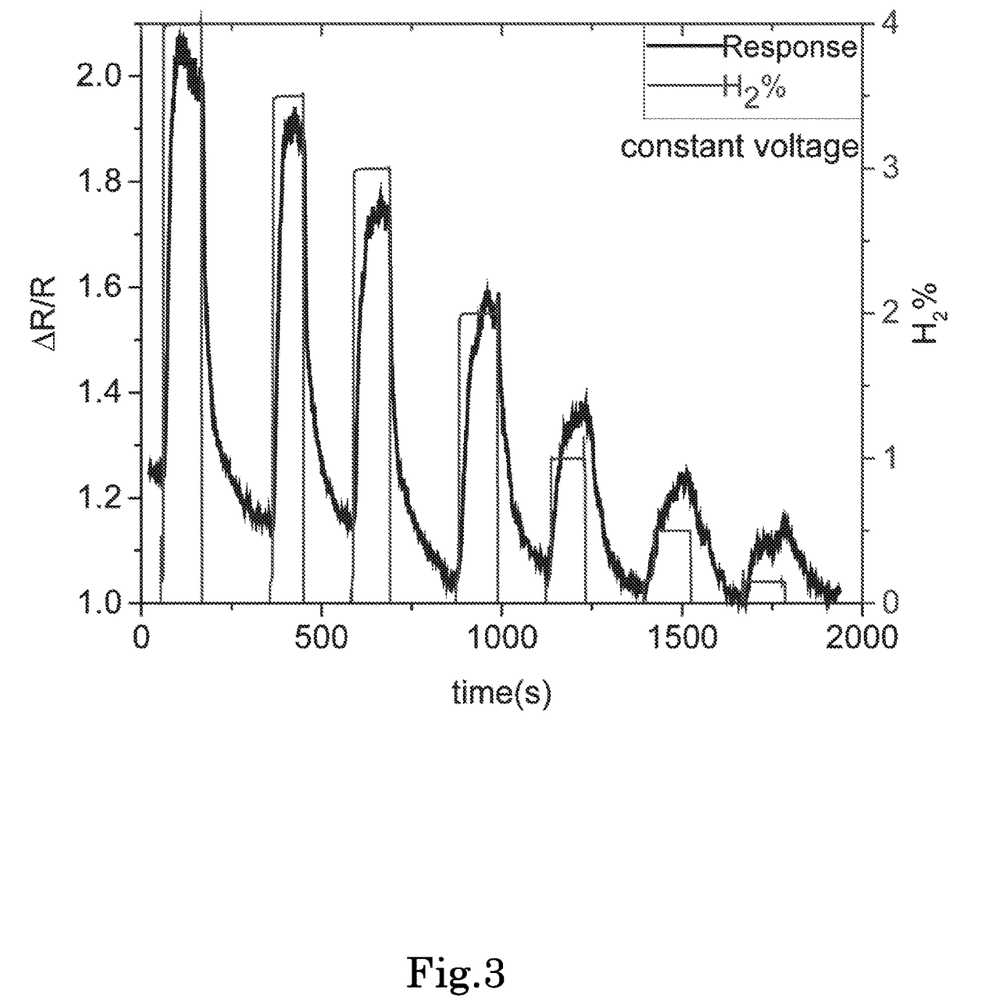
FIG. 3. demonstrates a response of a sensor according to one embodiment of the invention; the figure shows a response to an atmosphere containing 0.5 to 4.5% hydrogen in air.

FIG. 3 shows a sensor response to atmosphere containing hydrogen with concentration span of 0.5 to 4.5% hydrogen in air. The method for manufacturing a hydrogen sensor with the superior properties according to the invention was demonstrated by producing tens of active hydrogen sensors with low response time and high response amplitude.

Sensor Performance

Fabricated $H_2$ sensors responded to a range of $H_2$ concentration in air. For the bare PdNi sensor the concentration range was from 4% to 0.01% (100 ppm), for the PdNi-ITO the range was from 5% to 0.007% (70 ppm), and for the Pt-ITO the range was from 4% to 0.0125% (125 ppm). The sensors showed a quasi-linear electrical response to hydrogen at room temperature. The sensors were tested in a testing chamber connected to a gas channels system equipped with mass-flow controllers and electrical valves, with an interface to Labview software for automated measurements. The Au pads were connected with Cu wires and silver paste to a potentiostat.

Pd/Ni Sensor Performance

Figure 6A:
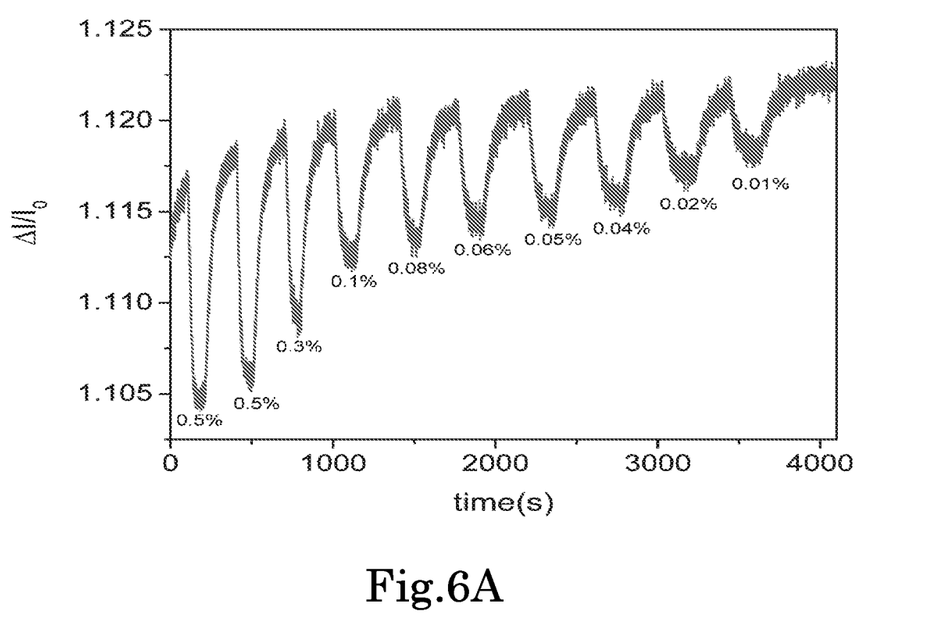
Figure 6B:
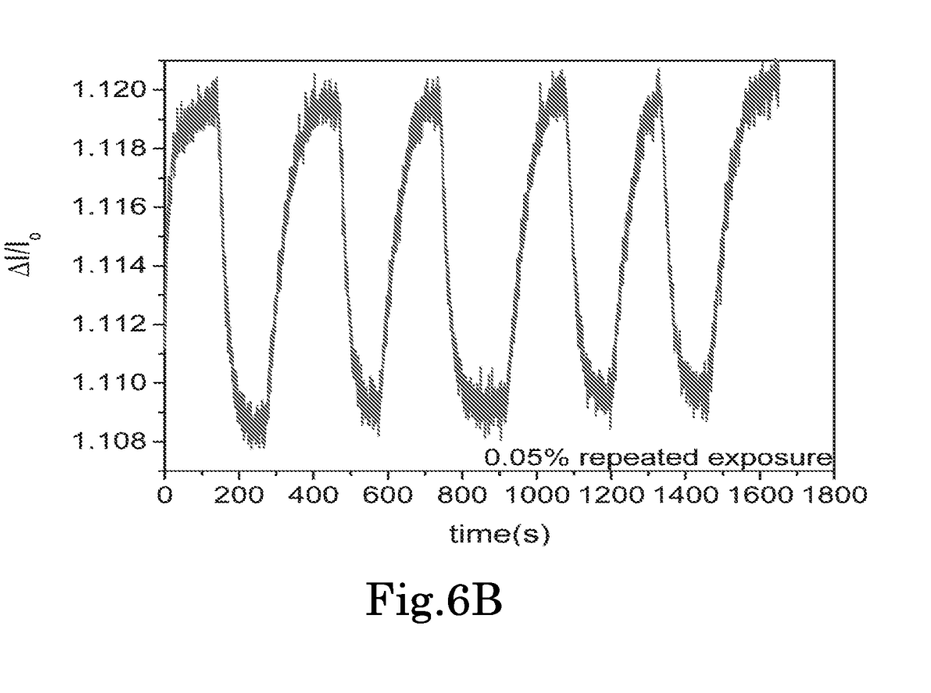
Figure 6C:
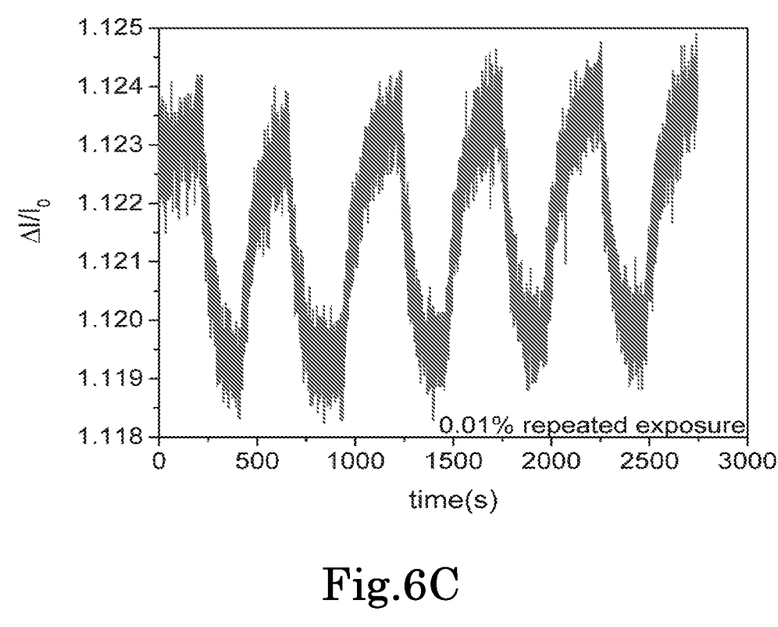

The electrical parameters were tuned to 7V in constant voltage mode. The electrical signals obtained were monitored and recorded. The analysis of the results revealed that the response time did not vary with the operation mode. On the other hand, the advantage of using the constant voltage mode arises from the response amplitude, with sharpened signals and lowered detection limit (FIG. 3). After initial tests were carried out, the sensors detection limit was checked with lower bias (0.5V). For this purpose, lower concentrations, ranging between 0.5-0.01% of $H_2$ were employed. The ability to detect lower concentration than the explosion limit (4% $H_2$) is critical for safety and hazard alarms. FIG. 6A shows the sensing results for the exposure of $H_2$ concentration range of 0.5% down to 100 ppm; the results indicate stable and sharp signals obtained while exposing the sensor to low $H_2$ concentration. While exposed to concentration above 0.1% $H_2$, the sensor signals displayed a slight drift. Exposing to lower concentration then 0.1% revealed more stable signal and faster recovery with a constant baseline. Moreover, the sensor response to 0.01% (100 ppm) $H_2$ showed a high and sharp amplitude, which might indicate the sensor ability to detect even lower $H_2$ concentration. The next step was to test the stability of the signal received from the sensor with repeated exposure to a low concentration. The sensor signals for repeated exposure of 500 ppm (FIG. 6B) and 100 ppm (FIG. 6C) did not show a significant drift. The sensor response was consistent, reproducible, and stable.

Figure 7:
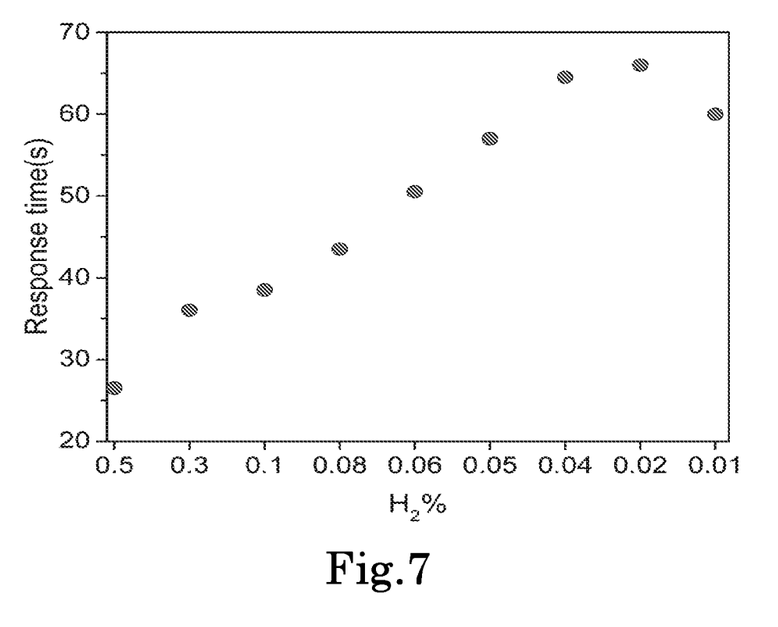
FIG. 7. the graph demonstrates the response time versus the $H_2$ concentration, in the range 0.5-0.01%, for one embodiment of sensor according to the invention.

Further, the response time of sensors manufactured according to the invention was characterized. The response time defines the time needed for the sensor to reach 90% of the signal amplitude. The NPs layer is expected to show a short response time due to its high surface area. Measured response times for the concentrations between 0.01 and 0.5% are shown in FIG. 7. An approximately inversely proportional behavior can be seen. The testing system (see also FIG. 5) was modified to exhibit shorter response times. Two electric valves very close to the testing chamber inlet were added, one for the air flow and one for the $H_2$, both interfaced to Labview. This modification addressed issues comprising mass-flow controller (MFC) response/stabilization time and leaking flow, which was crucial to avoid error sources. The leaking issue was solved by using the electric valve (open/close state) and the stabilization time was solved by initiating the MFC for several seconds with exhaust flow until it reached a stable and precise flow. At high $H_2$ concentration, constant current operation mode provided faster responses. The current set point was 0.1 mA and the measurements carried out with repeating exposure/washing of $H_2$/air with two flow rates of 100 and 50 ml/min.

The results are consistent with a response time of about 2.5 s for 100% $H_2$. It was found that there was no significant influence of the flow rate (pressure effect). The recovery time increased almost linearly with the flow rate. The recovery times were in the range 14-21 s for 100 ml/min, and in the range of 34-37 s for the lower flow rates.

Pd/Ni-ITO Sensor Performance

Figure 11A:
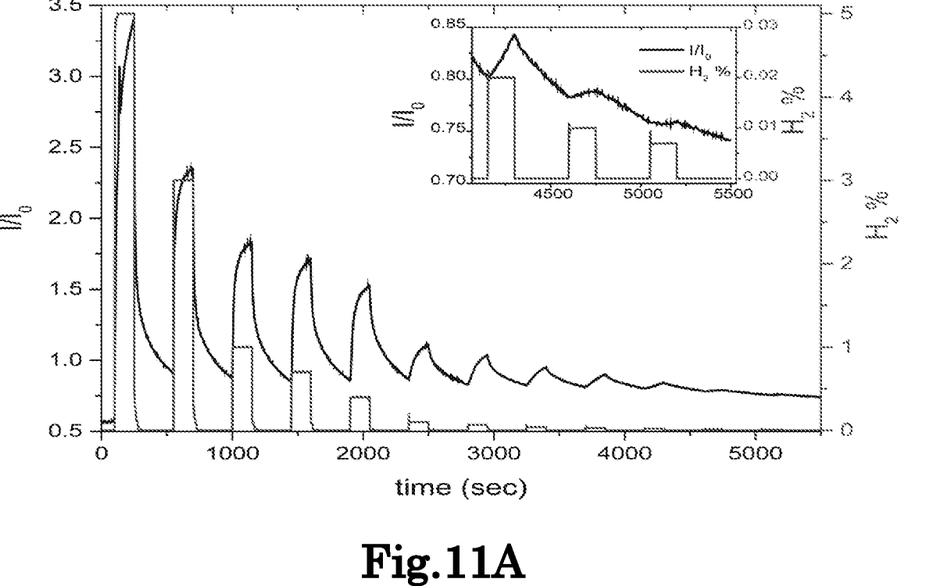
Figure 11B:
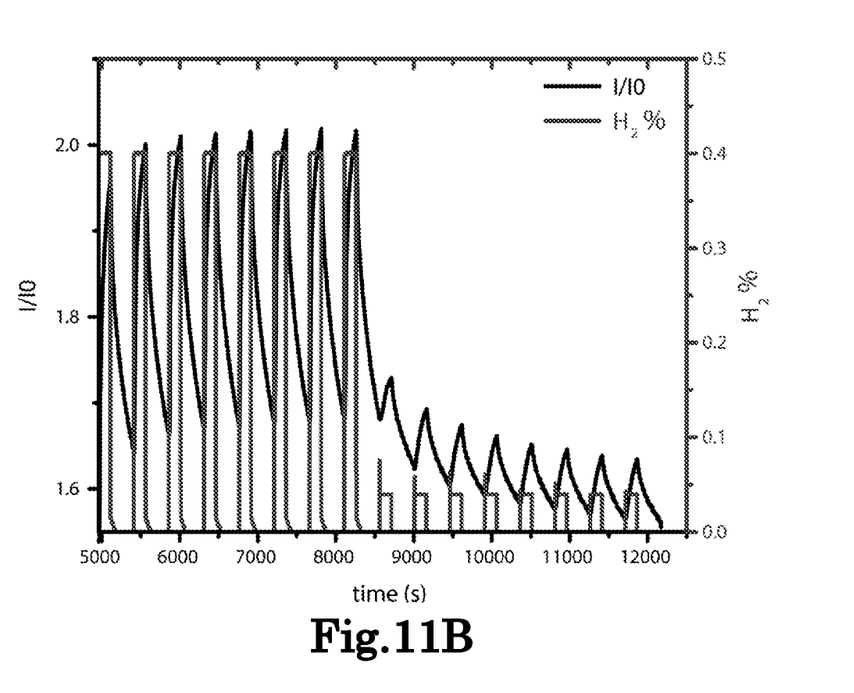

The electrical parameters were tuned to 0.3V in a constant voltage mode. The electrical signals obtained were monitored and recorded. The measurements ($H_2$ concentration and flow duration) was automated, using Labview, and the duration time of exposing/washing steps was set on 150/300 second, respectively. FIG. 11A shows the sensing results of the exposure of $H_2$ concentration range of 5% down to 70 ppm. Initially, while measuring the sensor signals with no $H_2$ exposure, the signal experience a slow decline. Exposing the sensor to $H_2$ is followed by a sharp increase (concentration dependent) even at a low concentration. When reaching the detection of 70 ppm of $H_2$, the signal was stabilized (FIG. 11A upper plot), instead of slightly decreasing as mentioned before. The next step was to test the stability of the signal due to repeated exposure of 0.4% and 400 ppm of $H_2$ and the results are showed in FIG. 11B; the sensor response was consistent, reproducible, and stable.

Pt-ITO Sensor Performance

Figure 12A:
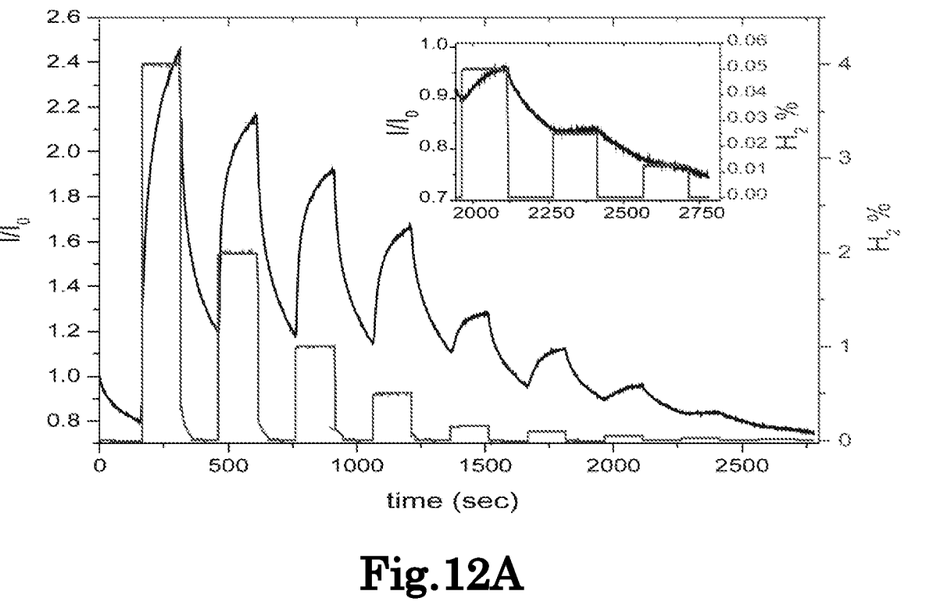
Figure 12B:
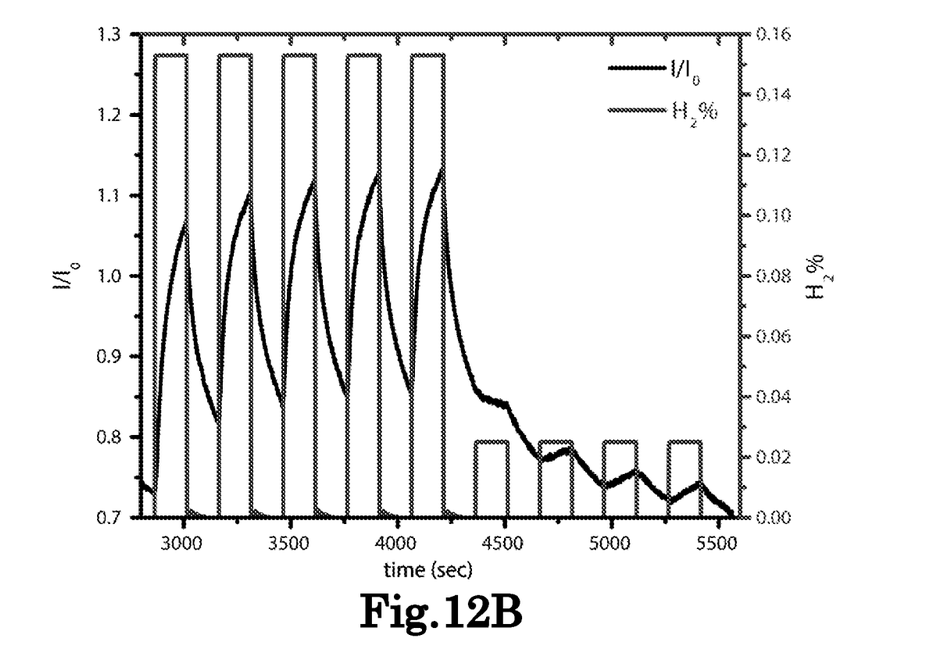
FIG. 12B shows the sensor behavior for a repeating exposure to $H_2$ mixture with the concentration of 0.15% and 0.025%.

The electrical parameters were tuned to 1V in constant voltage mode. The electrical signals obtained were monitored and recorded. The measurement ($H_2$ concentration and flow duration) was automated, using Labview, and the duration time of exposing/washing steps was set on 150/150 second, respectively. FIG. 12A shows the sensing results of the exposure to $H_2$ concentration range of from 4% down to 125 ppm; as in the PdNi-ITO case, the sensor experience a decline in the signal when not exposed to $H_2$ (FIG. 12A, inset); when reaching to 250 ppm of $H_2$, the response still had an increase in the signal. When near to 125 ppm, the signal could still be distinguished from the "base line" (sensor signal with no $H_2$ exposure). The next step was to test the stability of the signal due to repeated exposure of 0.4% and 400 ppm of $H_2$ and the results are presented in FIG. 12B. The signal was relatively high, compared to the "base line", and it was consistent, reproducible, and stable.

While the invention has been described using some specific examples, many modifications and variations are possible. It is therefore understood that the invention is not intended to be limited in any way, other than by the scope of the appended claims.

The invention claimed is:

1. A hydrogen sensor comprising metal nanoparticles as a resistive member in contact with two conductive electrodes, said electrodes constituted by a gold film, and said nanoparticles consisting of palladium and nickel (Pd/Ni) or platinum (Pt), the metal nanoparticles in the sensor with a size of less than 20 nm mixed with nanoparticles of a semiconductor with a size of less than 20 nm wherein said semiconductor nanoparticles and said metal nanoparticles are in a weight ratio of between about 1 and 200.

2. The sensor of claim 1, wherein said gold film is thinner than 200 nm.

3. The sensor of claim 1, wherein said semiconductor comprises zinc oxide, indium oxide, tin oxide, zinc tin oxide, or indium tin oxide (ITO).

4. The sensor of claim 1, adapted to sense hydrogen at a concentration in air of 0.1% or less.

5. The sensor of claim 1, wherein said resistive member comprises Pd/Ni, Pd/Ni with indium tin oxide (ITO), or Pt with ITO.

6. A hydrogen sensor comprising metal nanoparticles as a resistive member in contact with two conductive electrodes, said electrodes constituted by a gold film, and said nanoparticles consisting of palladium and nickel (Pd/Ni) or platinum (Pt), the metal nanoparticles in the sensor with a size of less than 20 nm mixed with nanoparticles of a semiconductor with a size of less than 20 nm; wherein said resistive member comprises Pd and Ni in a weight ratio of between 10 and 100.

7. A hydrogen sensor comprising:
   metal nanoparticles consisting of palladium and nickel (Pd/Ni) mixed with nanoparticles of a semiconductor; wherein said semiconductor nanoparticles and said metal nanoparticles are in a weight ratio of between about 1 and 200.

\* \* \* \* \*